(12) United States Patent
Joe et al.

(10) Patent No.: US 6,277,995 B1
(45) Date of Patent: Aug. 21, 2001

(54) PROCESS FOR PREPARATION OF 2-AMINOTHIAZOLECARBOXAMIDE DERIVATIVES

(75) Inventors: Goon-Ho Joe; Ju-Young Lee; Sang-Who Lee; Jae-Hoon Jeon; Kun-Tai Kim; Hwan-Sung Cheon, all of Yusong-ku (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/554,020

(22) PCT Filed: Sep. 10, 1999

(86) PCT No.: PCT/KR99/00535

§ 371 Date: May 10, 2000

§ 102(e) Date: May 10, 2000

(87) PCT Pub. No.: WO00/18766

PCT Pub. Date: Apr. 6, 2000

(30) Foreign Application Priority Data

Sep. 29, 1998 (KR) .............................................. 1998-40539

(51) Int. Cl.[7] .................................................. C07D 277/56
(52) U.S. Cl. ............................................................... 548/149
(58) Field of Search ................................................ 548/149

(56) References Cited

U.S. PATENT DOCUMENTS

| 4,399,075 | 8/1983 | Yoshida . |
| 5,514,643 | 5/1996 | Rew et al. . |

FOREIGN PATENT DOCUMENTS

| A1 292937 | 11/1988 | (EP) . |
| A2 313091 | 4/1989 | (EP) . |
| A2 434620 | 6/1991 | (EP) . |
| A1 639574 | 2/1995 | (EP) . |
| 0639574B1 | 6/1998 | (EP) . |
| 2614700 | 2/1997 | (JP) . |
| 124552 | 12/1997 | (KR) . |
| 212635 | 8/1999 | (KR) . |

OTHER PUBLICATIONS

Ra et al., Chemical Abstracts, vol. 124, No. 15, p. 1000 (1996).
Shell Internationale Research Maatschappij B. V., Chemical Abstracts, vol. 97, No. 1, p. 594 (1982).

*Primary Examiner*—Deborah C. Lambkin
*Assistant Examiner*—Sonya N. Wright

(57) ABSTRACT

A process for preparing a compound represented by formula (I), wherein $R^1$ represents straight-chain or branched $C_{1-5}$ alkyl, $C_{1-5}$ haloalkyl, or $C_{3-6}$ cycloalkyl, and $R^2$ represents $C_{1-3}$ alkyl or $C_{1-3}$ haloalkyl.

7 Claims, No Drawings

US 6,277,995 B1

PROCESS FOR PREPARATION OF 2-AMINOTHIAZOLECARBOXAMIDE DERIVATIVES

This application is the national phase under 35 U.S.C. § 371 of PCT International Application No. PCT/KR99/00535 which has an International filing date of Sep. 10, 1999, which designated the United States of America.

TECHNICAL FIELD

The present invention relates to a process for preparation of a 2-aminothiazolecarboxamide derivative represented by the following formula (I):

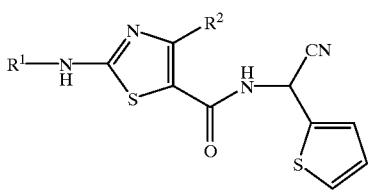

(I)

wherein $R^1$ represents straight-chain or branched $C_{1-5}$ alkyl, $C_{1-5}$ haloalkyl, or $C_{3-6}$ cycloalkyl, and $R^2$ represents $C_{1-3}$ alkyl or $C_{1-3}$ haloalkyl.

BACKGROUND ART

The compounds of formula (I) are used as microbicides for treating plant diseases caused by Pythiaceae or Peronosporaceae. The compounds of formula (I) were already disclosed in Korean Patent Laid-open Publication No. 94-19960 and the corresponding foreign applications, for example, U.S. Pat. application Ser. No. 08/287,917, JP Patent Application No. 192529 and EP Patent Application No. 94112652.6 which were filed by the present applicant.

Further, a process for preparation of 2-aminothiazolecarboxamide derivatives including the compounds of formula (I) using 2-aminothiazole carboxylic acid as an intermediate was described in Korean Patent Laid-open Publication No. 97-24120. However, this process has the disadvantage that it is not economic when applied to industrial production due to the many steps for obtaining the intermediate and the low yield.

Accordingly, the present inventors have studied to improve the prior process by solving the above mentioned problems, and as a result, have brought the present invention to completion.

DISCLOSURE OF THE INVENTION

The present invention relates to a process for preparation of a 2-aminothiazolecarboxamide derivative represented by the above formula (I) characterized in that an iminothiourea compound represented by the following formula (II):

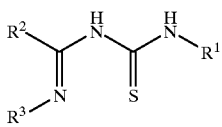

(II)

wherein $R^1$ and $R^2$ are defined as previously described, and $R^3$ represents phenyl which may be optionally mono- to penta-substituted independently by chloro, methoxy, ethoxy, phenoxy or nitro, is reacted with a thiopheneacetamide compound represented by the following formula (III):

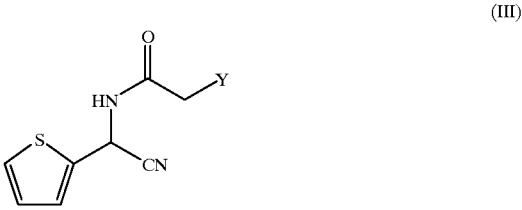

(III)

wherein Y represents a leaving group such as chloride, bromide, etc.

BEST MODE FOR CARRYING OUT THE INVENTION

The compound of formula (I) can be prepared by reacting the compound of formula (II) with the compound of formula (III) in a solvent and in the presence of a base as depicted in the following Reaction Scheme I:

[Reaction Scheme I]

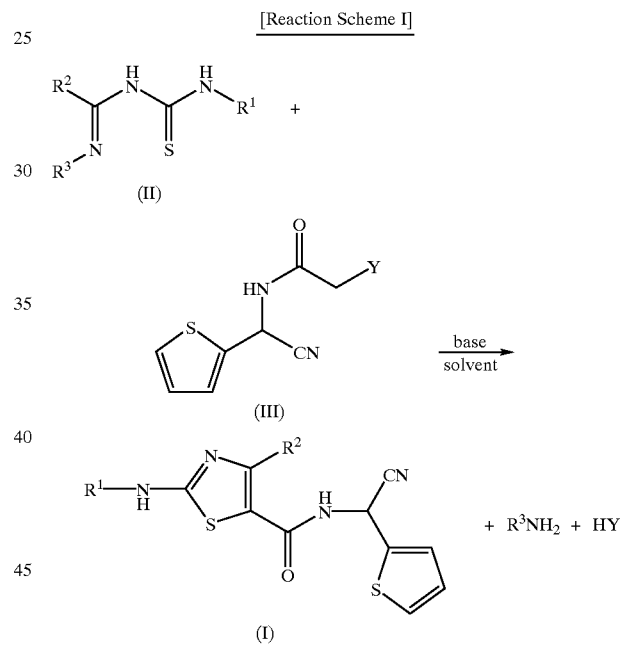

wherein $R^1$, $R^2$, $R^3$ and Y are defined as previously described.

Examples of the base used in the above reaction include an organic base such as triethylamine, tributylamine, diisopropylethylamine, N,N-dimethylaniline, pyridine, 4-dimethylaminopyridine, etc., and an inorganic base such as sodium hydroxide, potassium hydroxide, potassium carbonate, sodium hydrogencarbonate, potassium hydrogencarbonate, sodium hydride, potassium hydride, etc. The organic base is preferred, and the alkyl amine such as triethylamine, tributylamine, diisopropylethylamine, etc. is more preferred. The base can be used in an amount of 1 to 5 equivalents, preferably in an amount of 1 to 2 equivalents.

The above reaction can be carried out at the temperature between 20 and 120° C., preferably between 40 and 80° C., and the reaction time is suitably about 8 to 12 hours.

The solvent includes an alcohol such as methanol, ethanol, isopropyl alcohol, etc.; an aromatic hydrocarbon such as benzene, toluene, xylene, etc.; an ether such as diethylether, dioxane, 1,2-dimethoxyethane, tetrahydrofuiran, etc.; a ketone such as acetone, methylethyl ketone, cyclohexanone, etc.; a nitrile such as acetonitrile, propionitrile, etc.; a halogenated hydrocarbon such as dichloromethane, 1,2-dichloroethane, chloroform, etc.; an ester such as methyl acetate, ethyl acetate, etc.; and a polar solvent such as N,N-diethylformamide, N,N-dimethylacetamide, dimethyl sulfoxide, etc., and the alcohol is preferred.

The compound of formula (II) used as a starting material in the Reaction Scheme (I) is novel and can be prepared in accordance with the following Reaction Scheme (II):

[Reaction Scheme II]

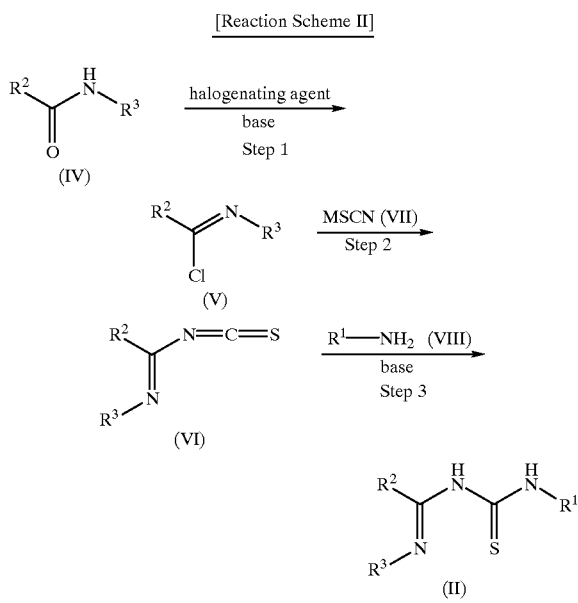

wherein $R^1$, $R^2$ and $R^3$ are defined as previously described.

That is, the compound of formula (II) can be prepared by a process characterized in that in Step 1, an amide compound represented by the following formula (IV):

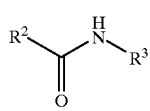

(IV)

wherein $R^2$ and $R^3$ are defined as previously described, is reacted with a halogenating agent in a solvent in the presence of a base to produce an imidoylchloride compound represented by the following formula (V):

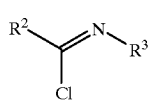

(V)

wherein $R^2$ and $R^3$ are defined as previously described;

in Step 2, the resulting imidoylchloride compound of formula (V) is reacted with an isothiocyanide compound represented by the following formula (VII):

MSCN (VII)

wherein M represents an alkali metal such as sodium, potassium, etc., or $NH_4$, by which the chloride group is replaced with the isothiocyanide group to produce an imidoylisothiocyanate compound represented by the following formula (VI):

(VI)

wherein $R^2$ and $R^3$ are defined as previously described;

in Step 3, the resulting imidoylisothiocyanate compound of formula (VI) is reacted with a primary amine compound represented by the following formula (VIII):

$R^1$—$NH_2$ (VIII)

wherein $R^1$ is defined as previously described, in the presence of a base.

In Step 1 for preparing the imidoylchloride compound of formula (V), thionyl chloride($SOCl_2$), phosgene($COCl_2$), phosphorus oxychloride($POCl_3$), etc. can be used as the halogenating agent. The halogenating agent is suitably used in an amount of 1 to 4 equivalents. This reaction is carried out at the temperature between −20° C. and 80° C., preferably between −10° C. and 20° C. The reaction time is suitably about 2 to 5 hours. As the base, an organic base such as pyridine, 4-dimethylaminopyridine, triethylamine, N,N-dimethyl aniline, tributylamine, etc. can be used. A mild base such as pyridine is preferred. The base is suitably used in an amount of 1 to 4 equivalents.

As the solvent, an aromatic hydrocarbon such as benzene, toluene, xylene, etc.; a halogenated hydrocarbon such as dichloromethane, 1,2-dichloroethane, chloroform, etc.; an ether such as diethylether, dioxane, 1,2-dimethoxyethane, tetrahydrofuran, etc.; a ketone such as acetone, methylethyl ketone, cyclohexanone, etc.; a nitrile such as acetonitrile, propionitrile, etc.; an ester such as methyl acetate, ethyl acetate, etc.; or a polar solvent such as N,N-dimethylformamide, N,N-dimethylacetamide, dimethyl sulfoxide, etc., preferably a halogenated hydrocarbon such as dichloroethane, chloroform, etc. can be used. In addition, N,N-dimethylfonrmamide can be used as a catalyst.

In Step 2, the imidoylisothiocyanate compound of formula (VI) is prepared by reacting the imidoylchloride compound of formula (V) prepared in step 1 with the isothiocyanide compound of formula (VII). The isothiocyanide compound of formula (VII) is suitably used in an amount of 1 to 2 equivalent. The reaction temperature can be between −20° C. and 50° C., preferably between 0° C. and 20° C., and the reaction time ranges suitably from 2 to 5 hours.

In Step 3, the iminothiourea compound of formula (II) is prepared from the imidoylisothiocyanate compound of formula (VI). In this step, the carbon atom of isothiocyanate is attacked by the amine compound of formula (VIII) in the presence of a base, by which the thiourea derivative of formula (II) is produced. The amine compound of formula (VIII) can be used in an amount of 1 to 4 equivalents, preferably 2 to 3 equivalents. This reaction can be carried out at the temperature between −20° C. and 80° C., preferably between 0° C. and 30° C. The reaction time is suitably from 2 to 4 hours.

The above processes according to the present invention will be more specifically explained through the following examples. As typical examples of the compounds of formula (II) according to the present invention, those described in the following table (I) can be mentioned.

TABLE I

| COM. NO. | R¹ | R² | R³ |
|---|---|---|---|
| 1 | ethyl | methyl | phenyl |
| 2 | ethyl | ethyl | phenyl |
| 3 | ethyl | ethyl | 2,6-dichlorophenyl |
| 4 | ethyl | ethyl | 4-methoxyphenyl |
| 5 | ethyl | ethyl | 4-phenoxyphenyl |
| 6 | ethyl | ethyl | 4-nitrophenyl |
| 7 | n-butyl | methyl | phenyl |
| 8 | n-butyl | ethyl | phenyl |
| 9 | isopropyl | ethyl | phenyl |
| 10 | isopropyl | methyl | phenyl |

The compound of formula (III) used as a starting material in the Reaction Scheme (I) is also a novel compound, and can be prepared in accordance with the following Reaction Scheme (III):

[Reaction Scheme III]

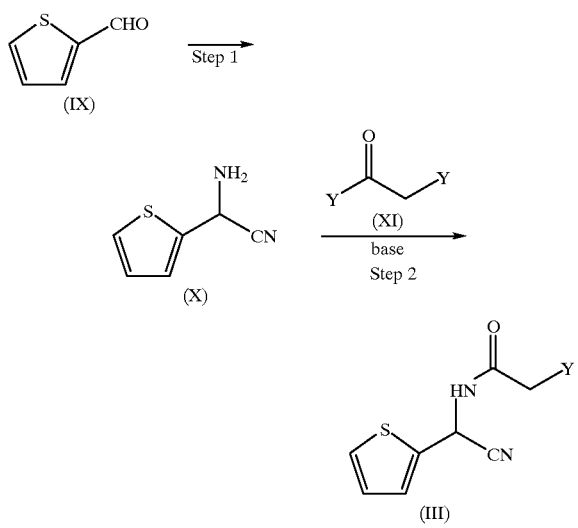

wherein Y is defined as previously described.

That is, the compound of formula (III) can be prepared by a process characterized in that in Step 1, an aldehyde compound represented by the following formula (IX):

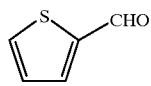

(IX)

is converted into an aminonitrile compound represented by the following formula (X):

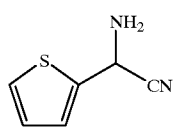

(X)

through the known Strecker Synthesis;

in Step 2, the resulting aminonitrile compound of formula (X) is reacted with a compound represented by the following formula (XI):

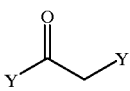

(XI)

wherein Y is defined as previously described, in the presence of a base.

In Step I of the above reaction, the aldehyde compound of formula (IX) can be readily converted into the aminonitrile compound of formula (X) through the known Strecker Synthesis as stated above.

In Step 2, the thiopheneacetamide compound of formula (III) can be prepared by reacting the aminonitrile compound of formula (X) with 1 to 3 equivalents, preferably 1 to 1.5 equivalents of chloroacetyl chloride or bromoacetyl bromide of formula (XI) in the presence of a base. This reaction can be carried out at the temperature between −20° C. and 80° C., preferably between 0° C. and 20° C. The reaction time is suitably from 30 minutes to 2 hours.

As the base, an organic base such as pyridine, 4-dimethylaminopyridine, triethylamine, N,N-dimethyl aniline, tributylamine, diisopropylethylamine, etc., preferably pyridine or 4dimethylamino pyridine can be used. The base can be suitably used in an amount of 1 to 3 equivalents.

As the solvent, a halogenated hydrocarbon such as dichloromethane, 1,2-dichloroethane, chloroform, etc.; an aromatic hydrocarbon such as bezene, toluene, xylene, etc.; an ether such as diethylether, dioxane, 1,2-dimethoxy ethane, tetrahydrofuran, etc.; a ketone such as acetone, methylethyl ketone, cyclohexanone, etc.; a nitrile such as acetonitrile, propionitrile, etc.; an ester such as methyl acetate, ethyl acetate, etc.; or a polar solvent such as N,N-dimethylformamide, N,N-dimethylacetamide, dimethyl sulfoxide, etc., preferably a halogenated hydrocarbon or an aromatic hydrocarbon can be used.

The present invention is more specifically explained by the following preparation and examples. However, it should be understood that the present invention is not limited to these examples in any manner.

PREPARATION 1:

Synthesis of N-phenyl-propionamide

Into a reaction vessel were placed aniline(279.4 g, 3.0 mol) and dichloromethane(2400g), the reaction vessel was cooled to 0° C., and sodium hydroxide(132.0 g, 3.3 mol) dissolved in water(660 g) was slowly added dropwise thereto.

It was confirmed that the temperature of the reaction vessel was 0° C., and then propionyl chloride(291.5 g, 3.2 mol) was added dropwise thereto for 2 hours. And then the mixture was stirred at room temperature(20° C.) for 2 hours, and the reaction was completed After the reaction was completed, the layers were separated, and dichloromethane was removed by distillation under the reduced pressure to produce a brown solid. The solid was recrystallized from toluene to give the title compound(434.7 g, 2.9 mol) in a yield of 97%.

$^1$H NMR (CDCl$_3$) : δ 7.75(1H, s, br), 7.52(2H, d), 7.29(2H, d), 7.08(1H, t), 2:37(2H, q), 1.22(3H, t)

EXAMPLE 1

Synthesis of N-ethyl-N'-(1-phenyliminopropyl)-thiourea

N-phenylpropionamide(149.2 g, 1.0 mol) and pyridine (261.0 g, 3.3 mol) were dissolved in dichloromethane(300 g), and the mixture was cooled to 0° C. Phosphorus oxychloride(168.7 g, 1.1 mol) was added dropwise thereto for 2 hours, and then the mixture was stirred at room temperature (20° C.) for 2 hours to produce N-phenylpropionimidoylchloride.

Subsequently, the reactant was slowly added dropwise to the reaction vessel containing the mixture of potassium isothiocyanide(145.8 g, 1.5 mol) and sodium carbonate (318.0 g, 3.0 mol) in acetone(1,000 ml,) at the temperature of 10° C. or less for 2 hours, and then the mixture was stirred for 1 hour to produce N-phenylpropionimidoyl isothiocyanate. Ethylamine(128.8 g, 2.0 mol) was added dropwise thereto maintaining the temperature of 10° C. or less for 2 hours, and then the mixture was stirred for 1 hour.

After the reaction was completed, the solvent was removed by distillation under reduced pressure. And the product was extracted by toluene and washed with sodium hydroxide solution. And then the toluene was removed by distillation under reduced pressure, and the residue was recrystallized from isopropyl alcohol to give the title compound(157.2 g, 0.7 mol) in a yield of 67%.

$^1$H NMR (CDCl$_3$): δ 11.84(1H, s, br), 8.18(1H, s, br), 7.32(2H, m), 7.12(1H, t), 6.79(2H, d), 3.69(2H, m), 2.23 (2H, q), 1.26(3H, t), 1.15(3H, t)

EXAMPLE 2

Synthesis of N-(1-(2,6-dichlorophenyl) iminopropyl))-N'-ethyl thiourea

N-(2,6-dichlorobenzene)propionamide(21.8 g, 0.1 mol) and pyridine(27.7 g, 0.35 mol) were dissolved in dichloromethane(30 g), and the mixture was cooled to 0° C. Phosphorus oxychloride(16.9 g, 0.11 mol) was added dropwise thereto for 2 hours, and then the mixture was stirred at room temperature (20° C.) for 2 hours to produce N-(2,6-dichloro benzene)propionimidoylchloride.

Subsequently, the reactant was slowly added dropwise to the reaction vessel containing the mixture of potassium isothiocyanide(14.6 g, 0.15 mol) and sodium carbonate(31.8 g, 0.3 mol) in acetone(100 ml) at the temperature of 10° C. or less for 2 hours, and then the mixture was stirred for 1 hour to produce N-(2,6-dichlorobenzene)propionimidoyl isothiocyanate. Ethylamine(12.9 g, 0.2 mol) was added dropwise thereto maintaining the temperature of 10° C. or less for 2 hours, and then the mixture was stirred for 1 hour.

After the reaction was completed, the title compound(21.9 g, 72 mmol) was obtained in a yield of 72% according to the same procedure as Example 1.

$^1$H NMR (CDCl$_3$): δ 8.69(1H, s, br), 8.65(1H, s, br), 7.43(1H, d), 7.21(1H, m), 6.78(1H, d), 3.70(2H, m), 2.23 (2H, q), 1.27(3H, t), 1.14(3H, t)

EXAMPLE 3

Synthesis of N-isopropyl-N'-(1-phenyliminopropyl) thiourea

N-phenylpropionamide(7.46 g, 0.05 mol) and pyridine (13.8 g, 0.18 mol) were dissolved in dichloromethane(300 g), and the mixture was cooled to 0° C. And then phosphorus oxychloride(8.43 g, 0.05 mol) was added dropwise thereto for 2 hours, and then the mixture was stirred at room temperature (20° C.) for 2 hours to produce N-phenylpropionimidoylchloride.

Subsequently, the reactant was slowly added dropwise to the reaction vessel containing the mixture of potassium isothiocyanide(7.3 g, 0.08 mol) and sodium carbonate(15.9 g, 0.15 mol) in acetone(50 ml) at the temperature of 10° C. or less for 2 hours, and then the mixture was stirred for 1 hour to produce N-phenylpropionimidoyl isothiocyanate. And isopropylamine(5.9 g, 0.1 mol) was added dropwise thereto maintaining the temperature of 10° C. or less for 2 hours, and then the mixture was stirred for 1 hour.

After the reaction was completed, the title compound(8.1 g, 0.03 mol) was obtained in a yield of 65% according to the same procedure as Example 1.

$^1$H NMR (CDCl$_3$): δ 11.80(1H, s, br), 7.92(1H, s, br), 7.35(2H, m), 7.13(1H, t), 6.79(2H, d), 4.50(1H, m), 2.25 (2H, q), 1.28(3H, s), 1.22(3H, s), 1.17 (3H, t)

EXAMPLE 4

Synthesis of 2-chloro-N-(α-cyano-2-thenyl) acetamide

Amino-thiophen-2-yl-acetonitrile hydrochloride(17.5 g, 0.1 mol) was dissolved in dichloromethane(100 ml), and then pyridine(16.6 g, 0.21 mol) was dropwise thereto. The mixture was cooled to 10° C., and then chloroacetyl chloride (12.4 g, 0.11 mol) was added dropwise thereto for 1 hour.

After the reaction was completed, the mixture was washed three times with each time water(60 ml), the solvent was removed by distillation under reduced pressure, and the residue was recrystallized from toluene to give the title compound(19.8 g, 0.09 mol) in a yield of 92%.

$^1$H NMR (CDCl$_3$): δ 7.42(1H, d), 7.32(1H, d), 7.23(1H, s, br), 7.05(1H, t), 6.28(1H, d), 4.15(2H, s)

EXAMPLE 5

Synthesis of 2-bromo-N-(α-cyano-2-thenyl) acetamide

Amino-thiophen-2-yl-acetonitrile hydrochloride(8.8 g, 0.05 mol) was dissolved in dichloromethane(50 ml), and then pyridine(8.7 g, 0.11 mol) was dropwise thereto. The mixture was cooled to 0° C., and then bromoacetyl bromide (10.1 g, 0.05 mol) was added dropwise thereto for 1 hour.

After the reaction was completed, the title compound(11.4 g, 0.04 mol) was obtained in a yield of 88% according to the same procedure as Example 4.

$^1$H NMR (CDCl$_3$): δ 7.41(1H, m), 7.32(1H, m), 7.11(1H, d, br), 7.05(1H, m), 6.25(1H, d), 3.94(2H, s)

EXAMPLE 6

Synthesis of N-(α-cyano-2-thenyl)-4-ethyl-2-(ethylamino)-5-thiazolecarboxamide

Method 1)

N-ethyl-N'-(1-phenyliminopropyl)thiourea(23.5 g, 0.1 mol) and 2-chioro-N-(α-cyano-2-thenyl)acetamide(21.4 g, 0.1 mol) were dissolved in methanol(200 ml). And then trietbylamine(15.2 g, 0.15 mol) was introduced therein, and the mixture was refluxed for 8 hours.

After the reaction was completed, the mixture was cooled and filtered. The residue was washed with cool methanol, and dried to give the title compound(24.0 g, 0.08 mol) in a yield of 75%.

Method 2)

N-(1-(2,6-dichlorophenyl)iminopropyl)-N'-ethylthiourea (3.1 g, 0.1 mol) and 2-chloro-N-(α-cyano-2-thenyl) acetamide(21.4 g, 0.1 mol) were dissolved in methanol(200 ml). And then triethylamine(15.2 g, 0.15 mol) was introduced therein, and the mixture was refluxed for 8 hours.

After the reaction was completed, the mixture was cooled by using cool methanol, and dried to give the title compound (24.0 g, 0.08 mol) in a yield of 75%.

$^1$H NMR (CDCl$_3$): δ 7.38(1H, d), 7.33(1H, d), 7.04(1H, t), 6.43(1H, d), 5.94(1H, d, br), 5.59(1H, s, br), 3.26(2H, q), 2.93(2H, q), 1.26(6H, m)

EXAMPLE 7

Synthesis of N-(α-cyano-2-thenyl)-2-(ethylamino)-4-methyl-5-thiazolecarboxamide N-ethyl-N'-(1-phenyliminopropyl)thiourea(22.1 g, 0.1 mol) and 2-chloro-N-(α-cyano-2-thenyl)acetamide(21.4 g, 0.1 mol) were dissolved in ethanol(200 ml). And then diisopropylethylamine(15.5 g, 0.12 mol) was introduced therein, and the mixture was stirred at the temperature of 60° C. for 10 hours.

After the reaction was completed, the solvent was removed by distillation under reduced pressure to produce a brown solid. The solid was recrystallized from the mixture solution of toluene and water (v/v=10/1) to give the title compound(22.1 g, 0.07 mol) in a yield of 72%.

$^1$H NMR (CDCl$_3$): δ 7.36(1H, d), 7.30(1H, d), 7.04(1H, t), 6.10(1H, d), 5.99(1H, s, br), 3.28(2H, q), 2.53(3H, s), 1.30(3H, t)

EXAMPLE 8

Synthesis of N-(α-cyano-2-thenyl)-4-ethyl-2-(isopropylamino)-5-thiazolecarboxamide N-isopropyl-N'-(1-phenyliminopropyl)thiourea(2.5 g, 0.01 mol) and 2-bromo-N-(α-cyano-2-thenyl)acetamide(2.6 g, 0.01 mol) were dissolved in methanol(20 ml). And then triethylamine(1.5 g, 0.02 mol) was introduced therein, and the mixture was stirred at the temperature of 60° C. for 7 hours.

After the reaction was completed, the solvent was removed by distillation under reduced pressure to produce a brown solid. The solid was recrystallized from the mixture solution of ethanol and water (v/v=1/1) to give the title compound(2.0 g, 0.01 mol) in a yield of 60%.

$^1$H NMR (CDCl$_3$): δ 7.38(1H, d), 7.30(1H, d), 7.01(1H, t), 6.44(1H, d), 6.00(1H, d), 5.49(1H, s, br), 3.61(1H, m), 2.91(2H, q), 1.27(9H, m)

As described above, a 2-aminothiazolecarboxamide derivative of formula (I) can be prepared by using the intermediates of formulae (II) and (III) in the high yield, according to the process of the present invention. And the present process is more economic than the conventional process because of the high yield from the industrial viewpoint.

What is claimed is:

1. A process for preparing a compound represented by the following formula (I):

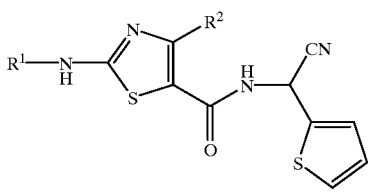

(I)

wherein R$^1$ represents straight-chain or branched C$_{1-5}$ alkyl, C$_{1-5}$ haloalkyl, or C$_{3-6}$ cycloalkyl, and R$^2$ represents C$_{1-3}$ alkyl or C$_{1-3}$ haloalkyl, characterized in that a compound represented by the following formula (II):

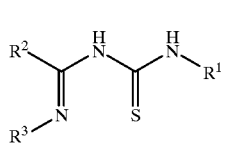

(II)

wherein R$^1$ and R$^2$ are defined as previously described, and R$^3$ represents phenyl which may be optionally mono- to penta-substituted independently by chloro, methoxy, ethoxy, phenoxy or nitro, is reacted with a compound represented by the following formula (III):

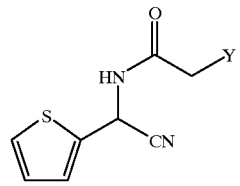

(III)

wherein Y represents a leaving group, in a solvent and in the presence of a base.

2. The process according to claim 1, wherein Y represents chloride or bromide.

3. The process according to claim 1, wherein the solvent is an alcohol selected from a group consisting of methanol, ethanol and isopropyl alcohol; an aromatic hydrocarbon selected from a group consisting of benzene, toluene and xylene; an ether selected from a group consisting of diethylether, dioxane, 1,2-dimethoxyethane and tetrahydrofuran; a ketone selected from a group consisting of acetone, methylethyl ketone and cyclohexanone; a nitrile selected from a group consisting of acetonitrile and propionitrile; a halogenated hydrocarbon selected from a group consisting of dichloromethane, 1,2-dichloroethane and chloroform; an ester selected from a group consisting of methyl acetate and ethyl acetate; or a polar solvent selected from a group consisting of N,N-diethylformamide, N,N-dimethylacetamide and dimethyl sulfoxide.

4. The process according to claim 3, wherein the solvent is the alcohol.

5. The process according to claim 1, wherein the base is an organic base selected from a group consisting of triethylamine, tributylamine, diisopropylethylamine, N,N-dimethylaniline, pyridine and 4-dimethylamino pyridine, or an inorganic base selected from a group consisting of sodium hydroxide, potassium hydroxide, potassium carbonate, sodium hydrogencarbonate, potassium hydrogencarbonate, sodium hydride and potassium hydride.

6. The process according to claim 5, wherein the base is the organic base.

7. The process according to claim 1, wherein the reaction is carried out at the temperature between 20° C. and 120° C. for 8 to 12 hours.

* * * * *